(12) United States Patent
Ritchie et al.

(10) Patent No.: US 6,945,927 B1
(45) Date of Patent: Sep. 20, 2005

(54) SEXUAL AID

(76) Inventors: Steven D. Ritchie, 4700 95th St. North, St. Petersburg, FL (US) 33708; Harlie David Reynard, 5054 Johns Pass Ave., Madeira Beach, FL (US) 33708

( * ) Notice: Subject to any disclaimer, the term of this patent is extended or adjusted under 35 U.S.C. 154(b) by 0 days.

(21) Appl. No.: 10/782,354

(22) Filed: Feb. 19, 2004

Related U.S. Application Data

(63) Continuation-in-part of application No. 10/060,997, filed on Feb. 1, 2002, now abandoned.

(51) Int. Cl.[7] .............................................. A61F 5/00
(52) U.S. Cl. ...................................................... 600/38
(58) Field of Search ................... 600/38–41; D24/214, D24/285

(56) References Cited

U.S. PATENT DOCUMENTS

| | | | | |
|---|---|---|---|---|
| 3,996,930 A | * | 12/1976 | Sekulich | 601/137 |
| 5,690,603 A | * | 11/1997 | Kain | 600/38 |
| 5,853,362 A | * | 12/1998 | Jacobs | 600/38 |
| 6,132,366 A | * | 10/2000 | Ritchie et al. | 600/38 |
| 6,533,718 B1 | * | 3/2003 | Ritchie et al. | 600/38 |

* cited by examiner

*Primary Examiner*—Samuel G. Gilbert
(74) *Attorney, Agent, or Firm*—Edward P. Dutkiewicz

(57) ABSTRACT

A sexual aid system. A head portion in a bi-lobar configuration with a right lobe and a left lobe. A shaft portion is adjacent to the head portion with a gripping portion.

2 Claims, 3 Drawing Sheets

SEXUAL AID

RELATED APPLICATION

The present patent application is a continuation-in-part of application Ser. No. 10/060,997 filed Feb. 1, 2002, now abandon.

BACKGROUND OF THE INVENTION

1. Field of the Invention

The present invention relates to a sexual aid and more particularly pertains to allowing a user to stimulate the upper vaginal wall without impinging on the therein contained urethra.

2. Description of the Prior Art

The use of sex devices is known in the prior art. More specifically, sex devices previously devised and utilized for the purpose of sexual stimulation and/or exercise are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 3,996,930 to Sekuliuch issued Dec. 14, 1976 and relates to a self-contained gynecologic stimulator. U.S. Pat. No. 5,853,362 to Jacobs issued Dec. 29, 1998 and relates to glandular stimulator device and method. U.S. Pat. No. 6,059,707 to Dabney issued May 9, 2000 and relates to a sexual aid. Lastly, U.S. Pat. No. Des. 384,156, a design patent, to Kain issued Sep. 23, 1997 and relates to an erogenic stimulator.

While these devices fulfill their respective, particular objectives and requirements, the aforementioned patents do not describe sexual aid that allows allowing a user to stimulate the upper vaginal wall without impinging on the therein contained urethra.

In this respect, the sexual aid according to the present invention substantially departs from the conventional concepts and designs of the prior art, and in doing so provides an apparatus primarily developed for the purpose of allowing a user to stimulate the upper vaginal wall without impinging on the therein contained urethra.

Therefore, it can be appreciated that there exists a continuing need for a new and improved sexual aid which can be used for allowing a user to stimulate the upper vaginal wall without impinging on the therein contained urethra. In this regard, the present invention substantially fulfills this need.

SUMMARY OF THE INVENTION

In view of the foregoing disadvantages inherent in the known types of sex devices now present in the prior art, the present invention provides an improved sexual aid. As such, the general purpose of the present invention, which will be described subsequently in greater detail, is to provide a new and improved sexual aid and method which has all the advantages of the prior art and none of the disadvantages.

To attain this, the present invention essentially comprises a sexual aid system for allowing a user to stimulate the upper vaginal wall without impinging on the therein contained urethra therein contained urethra. The system comprises, in combination, a head portion having a bi-lobar configuration with a right lobe and a left lobe and a groove formed there between. The head has a first external diameter. The system also comprises a shaft portion comprising a length having a generally solid tubular configuration having a second external diameter. The shaft portion is adjacent to the head portion. Lastly, a gripping portion has a generally solid tubular configuration with a second external diameter. The gripping portion is adjacent to the shaft portion and opposite the head portion.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved sexual aid which has all of the advantages of the prior art sex devices and none of the disadvantages.

It is another object of the present invention to provide a new and improved sexual aid which may be easily and efficiently manufactured and marketed.

It is further object of the present invention to provide a new and improved sexual aid which is of durable and reliable constructions.

An even further object of the present invention is to provide a new and improved sexual aid which is susceptible of a low cost of manufacture with regard to both materials and labor, and which accordingly is then susceptible of low prices of sale to the consuming public, thereby making such sexual aid economically available to the buying public.

Even still another object of the present invention is to provide a sexual aid for allowing a user to stimulate the upper vaginal wall without impinging on the therein contained urethra.

Lastly, it is an object of the present invention to provide a new and improved sexual aid system comprising a head portion having a bi-lobar configuration with a right lobe and a left lobe; a shaft portion being adjacent to the head portion; and a gripping portion.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
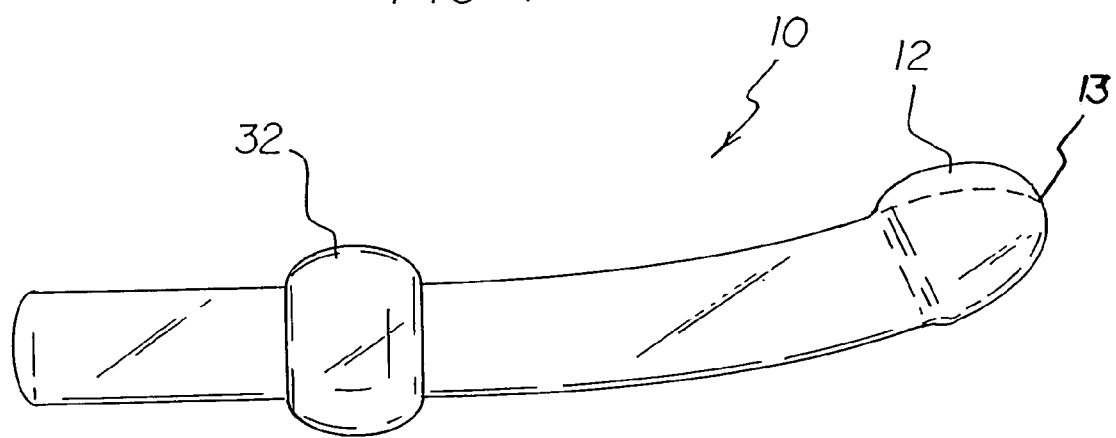
FIG. 1 is a side elevational view of a sexual aid constructed in accordance with the principles of the present invention.
Figure 2:
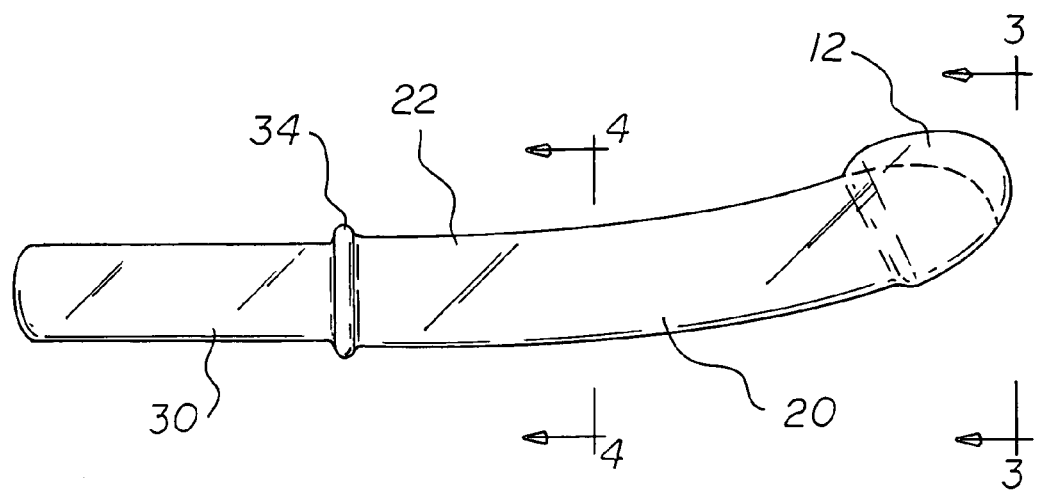
FIG. 2 is a side elevational view of a sexual aid constructed in accordance with another embodiment of the present invention.
Figure 3:
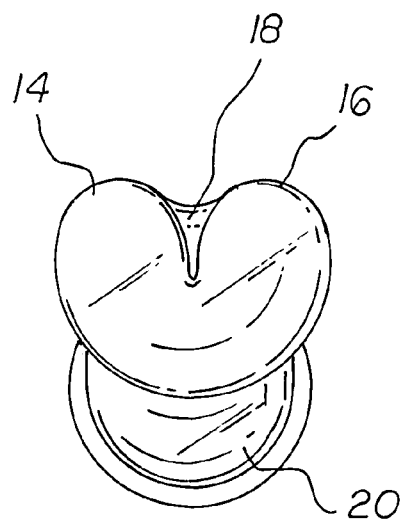
FIG. 3 is a front elevational view taken along line 3—3 of FIG. 2.
Figure 4:
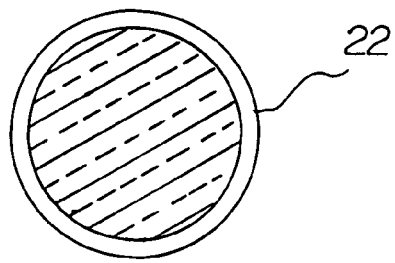
FIG. 4 is a cross sectional view taken along line 4—4 of FIG. 2.
Figure 5:
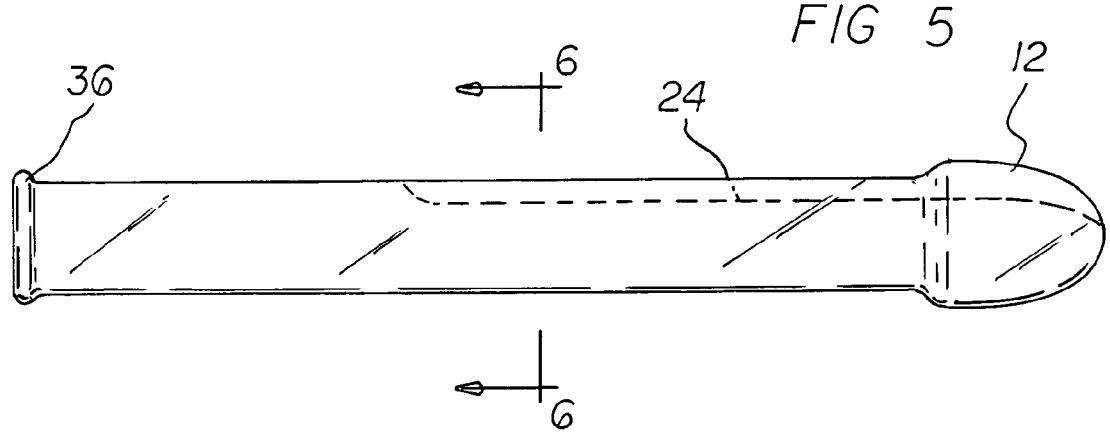
FIG. 5 is a side elevational view of another sexual aid constructed in accordance with yet another embodiment of the present invention.
Figure 6:
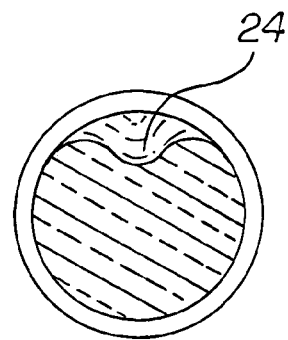
FIG. 6 is a cross sectional view taken along line 6—6 of FIG. 5.

With reference now to the drawings, and in particular to FIG. 1 thereof, the preferred embodiment of the new and improved sexual aid embodying the principles and concepts of the present invention and generally designated by the reference numeral 10 will be described.

The present invention, the sexual aid 10 is comprised of a plurality of components. Such components in their broadest context include a head portion, a shaft portion, and a gripping portion. Such components are individually configured and correlated with respect to each other so as to attain the desired objective.

The sexual aid system 10 of the present invention functions for allowing a user to stimulate the upper vaginal wall without impinging on the therein contained urethra. The system comprises several components, in combination.

First provided is a head portion 12. The head portion has a bi-lobar configuration with a right lobe 14 and a left lobe 16 and a linearly configured groove 18 formed there between. The head has a tip 13. The groove runs the length of the head, from the outermost extent, or tip, inwards. The head has a first external diameter.

It is understood by one skilled in the art that the configuration of the head portion can take any one of a plurality of forms, including being rounded, lobularly shaped and configurations having a tapered tip.

Next provided is a shaft portion 20. The shaft portion comprises a length 22. The shaft has a generally solid tubular configuration and has a second external diameter. The second external diameter is smaller than the first external diameter. The shaft portion is located adjacent to the head portion.

In an alternate embodiment the shaft may have a groove extending part of or entirely down the length 24 of the shaft.

Last provided is a gripping portion 30. The gripping portion has a generally solid tubular configuration with a second external diameter. The gripping portion is located adjacent to the shaft portion and opposite the head portion.

In an alternate embodiment the gripping portion may have at least one raised area 32 to promote the user's gripping of that portion.

In another alternate embodiment the gripping portion may also have a flange 34 located between the gripping portion and the shaft portion.

In still another alternate embodiment the gripping portion may also have a flange 36 located at the end of the gripping portion.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A sexual aid system for allowing a user to stimulate the upper vaginal wall without impinging on the therein contained urethra, comprising in combination:
   a head portion having a bi-lobar configuration with a right lobe and a left lobe, the head portion having a tip with a linearly configured groove formed there between with the groove running the length of the head, from the tip of the head portion and inwardly, the head having a first external diameter;
   a shaft portion comprising a length having a generally solid tubular configuration having a second external diameter, with the second external diameter being smaller than the first external diameter, the shaft portion being adjacent to the head portion with the shaft having a groove running contiguous with the groove of the bi-lobar head portion and running linearly along the length of the shaft from the outermost end of the head portion to the gripping portion; and
   a gripping portion having a generally solid tubular configuration with a diameter being the same as the second external diameter, the gripping portion being adjacent to the shaft portion and opposite the head portion.

2. A sexual aid system comprising:
   a head portion having a bi-lobar configuration with a right lobe and a left lobe, the head portion having a length, the head portion also having a groove running between the lobes, the groove running the length of the head portion, the head having a first external diameter;
   a shaft portion being adjacent to the head portion, the shaft comprising a length having a generally solid tubular configuration having a second external diameter, the shaft having a groove running contiguous with the groove of the bi-lobar head portion; and
   a gripping portion adjacent to the shaft portion and opposite the head portion and the gripping portion further including an enlarged annular flange between the shaft portion adn the gripping portion;
   the sexual aid being fabricated of borosilicate glass, the glass having an appreciate amount of oxide of boron to enhance the lubricity of the sexual aid system.

* * * * *